(12) United States Patent
Wehowski et al.

(10) Patent No.: US 7,630,084 B2
(45) Date of Patent: Dec. 8, 2009

(54) SYSTEM AND METHOD FOR ACQUIRING AND EVALUATING OPTICAL SIGNALS

(75) Inventors: Frederic Wehowski, Hockenheim (DE); Bern Rosicke, Mannheim (DE); Stefan Kalveram, Viernheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 284 days.

(21) Appl. No.: 11/871,185

(22) Filed: Oct. 12, 2007

(65) Prior Publication Data
US 2008/0259339 A1 Oct. 23, 2008

(30) Foreign Application Priority Data
Oct. 14, 2006 (EP) .................................. 06021584

(51) Int. Cl.
*G01B 9/02* (2006.01)
(52) U.S. Cl. ...................................... 356/484
(58) Field of Classification Search .................. 356/433, 356/484
See application file for complete search history.

(56) References Cited

U.S. PATENT DOCUMENTS

| 4,553,848 | A | 11/1985 | Rösicke et al. |
| 5,463,467 | A | 10/1995 | Baumann et al. |
| 6,562,625 | B2 | 5/2003 | Modzelewski et al. |
| 6,574,425 | B1 | 6/2003 | Weiss et al. |
| 7,030,381 | B2 | 4/2006 | Kilian et al. |
| 7,230,712 | B2 * | 6/2007 | Cannon ....................... 356/437 |
| 7,426,038 | B2 * | 9/2008 | Ogawa ........................ 356/484 |

FOREIGN PATENT DOCUMENTS

| DE | 197 08 216 A1 | 9/1998 |
| DE | 199 11 325 C1 | 7/2000 |
| JP | 58225345 | 12/1983 |
| WO | WO 01/22871 | 4/2001 |

\* cited by examiner

*Primary Examiner*—Michael A Lyons
(74) *Attorney, Agent, or Firm*—Baker & Daniels LLP

(57) ABSTRACT

A system and method for measuring and evaluating optical signals for detecting an analyte in an analysis liquid.

21 Claims, 1 Drawing Sheet

SYSTEM AND METHOD FOR ACQUIRING AND EVALUATING OPTICAL SIGNALS

RELATED APPLICATIONS

The present case is a US Nationalization of EP 06021584.5, filed Oct. 14, 2006, the disclosure of which is incorporated herein by reference.

FIELD

The present invention relates to a system for acquiring and evaluating optical signals. The present invention more particularly relates to a system for detecting an analyte in an analysis liquid via optical analysis.

BACKGROUND AND SUMMARY

Analysis systems, which operate using photometric signals and in which test carriers tailored to the analysis devices are used, are employed to determine an analyte in an analysis liquid, in particular in bodily fluids such as blood for the purpose of medical testing. The test carriers (which are also referred to as analysis elements) are usually implemented in form of test strips. They typically have one or more test panels, which comprise at least one test layer. The test layer contains one or more reagents. When an analysis liquid is applied, a chemical reaction of the constituents of the analysis liquid occurs, which results in a detectable change of the test panel, in particular in a color change. This change is analyzed using suitable methods. For example, in a reflection photometry measurement, the concentration of a constituent of the analysis liquid to be determined may be concluded from the diffuse reflectance of the test panel after completion of the chemical reaction. In other cases, the desired result may be derived from the chronological change of the reflectivity.

Other analysis systems operating using optical analysis are also known, in particular systems with test carriers which are implemented as capillary test strips. In this case, the reagents are located in a capillary channel which also has an optical measuring zone. Moreover, systems having optical reference channels are also known, as well as systems which operate on the base of fluorescence measurements.

The system has a test carrier, which has an optical evaluation zone. The system comprises a light source for illuminating the optical evaluation zone on the test carrier, a signal generator for generating a first control signal the first control signal having a frequency F1 and an intensity I1, and a light sensor for receiving light remitted from the optical valuation zone, and for converting it into a measuring signal. The measuring signal and the first control signal of the signal generator are fed to a first frequency-selective amplifier. A first output signal is outputted at the output of the amplifier.

Furthermore, the present invention is directed to a method for acquiring and evaluating optical signals. Light received by a light sensor is converted into a measuring signal, which is fed to a frequency-selective amplifier.

The present invention is directed to optical analysis systems of arbitrary construction, insofar as they use test carriers having an optical evaluation zone, in which an optically measurable change is detected using light-optical measuring methods as a measure of the desired analytical result. These are primarily photometric methods, in which light irradiated onto the optical evaluation zone is diffusely reflected. However, the present invention is also additionally suitable for fluorescence measurements. The optical evaluation zone is also referred to in many cases as a "test panel". This term is also used in the following to identify the optical evaluation zone without restricting the generality.

The measurement and evaluation of the optical signals demands especially high requirements on the precision, to determine the very small measuring currents or voltages with sufficient resolution and allow a quantitative analysis. The measurements are influenced by multiple interference sources, which include the typical problems when measuring small signals. These are, for example, amplifier drift or superimposed DC or AC voltages, in particular low-frequency interfering voltages, as well as interfering currents of various types.

In addition to these interferences, optical interferences due to external light exist. These include constant external light components and modulated interferences, in particular from utility-operated external light sources, which act at the typical utility frequencies and their harmonic.

Analysis devices having test carriers, which reduce the entry of external light into the measuring area of the device, in particular onto the optical evaluation zone, by constructive measures, are known. These devices have a narrow channel, in which the test carrier is inserted into the housing interior. Another embodiment has a cover which is closed after introduction of the test strip and before beginning the measurement.

In addition to the constructive mechanical suppression of the interfering light, systems are known in which an electronic suppression of the interference by external light is performed. For example, WO 01/22871 A1 discloses an optical glucose measuring system, in which a frequency-selective amplifier in the form of a lock-in amplifier is used. On one hand, the lock-in amplifier is fed by the measuring signal of a magneto-optical sensor. On the other hand, it receives a signal of an external signal generator having a predefined frequency as a reference signal. The signal component of the measuring signal whose frequency corresponds to the reference signal of the signal generator is thus selectively amplified. Filtering for a specific frequency is thus performed by using the lock-in amplifier. Interfering light having frequencies, which differ from the frequency of the reference signal, is not amplified or is only amplified strongly damped and is thus not taken into consideration or is only taken into consideration correspondingly reduced in the measurement. To further improve this system, it is suggested that two lock-in amplifiers be connected in series. The output signal of the first lock-in amplifier is thus fed to the second lock-in amplifier. The signal to noise ratio of the sensor is thereby further improved. However, if an interference has the frequency of the reference signal, the interfering signal is also amplified and an incorrect measurement result is output. The occurrence of interference and the corruption of the measurement results can not be recognized by the system.

The use of lock-in amplifiers and the combination of multiple amplifiers, as well as a cascaded serial connection of two amplifiers is known, for example, from "Application Note AN1003, Low Level Optical Detection using Lock-In Amplifier Techniques" from "AMETEK Signal Recovery".

Another pathway is followed by the methods disclosed in U.S. Pat. No. 5,463,467 (DE 43 21 548 A1) and U.S. Pat. No. 4,553,848 (DE 3138879 A1) for acquiring and evaluating analog photometric signals, in which the test panel of a test carrier is irradiated by a light source cycled in light-dark phases. The remitted light is recorded and integrated by a measuring receiver during a measuring period comprising multiple light-dark phases. Effective interference and external light suppression, which allows measurement even without the shielding against ambient light typical up to this point, is achieved by an irregular sequence of the light and dark phases integrated during the measuring period. The sequence is irregular in such a manner that the Fourier-transformed frequency spectrum contains multiple different frequencies, so that each individual frequency enters into the measuring result as a small fraction. Corresponding interfering frequencies can thus act on the corruption of the measuring result with a fractional error contribution.

The present invention provides suppression of interfering signals in the measurement and evaluation of optical signals to determine an analyte in an analysis liquid and to increase the reliability of the determination.

DETAILED DESCRIPTION OF THE DRAWINGS

Figure 1:
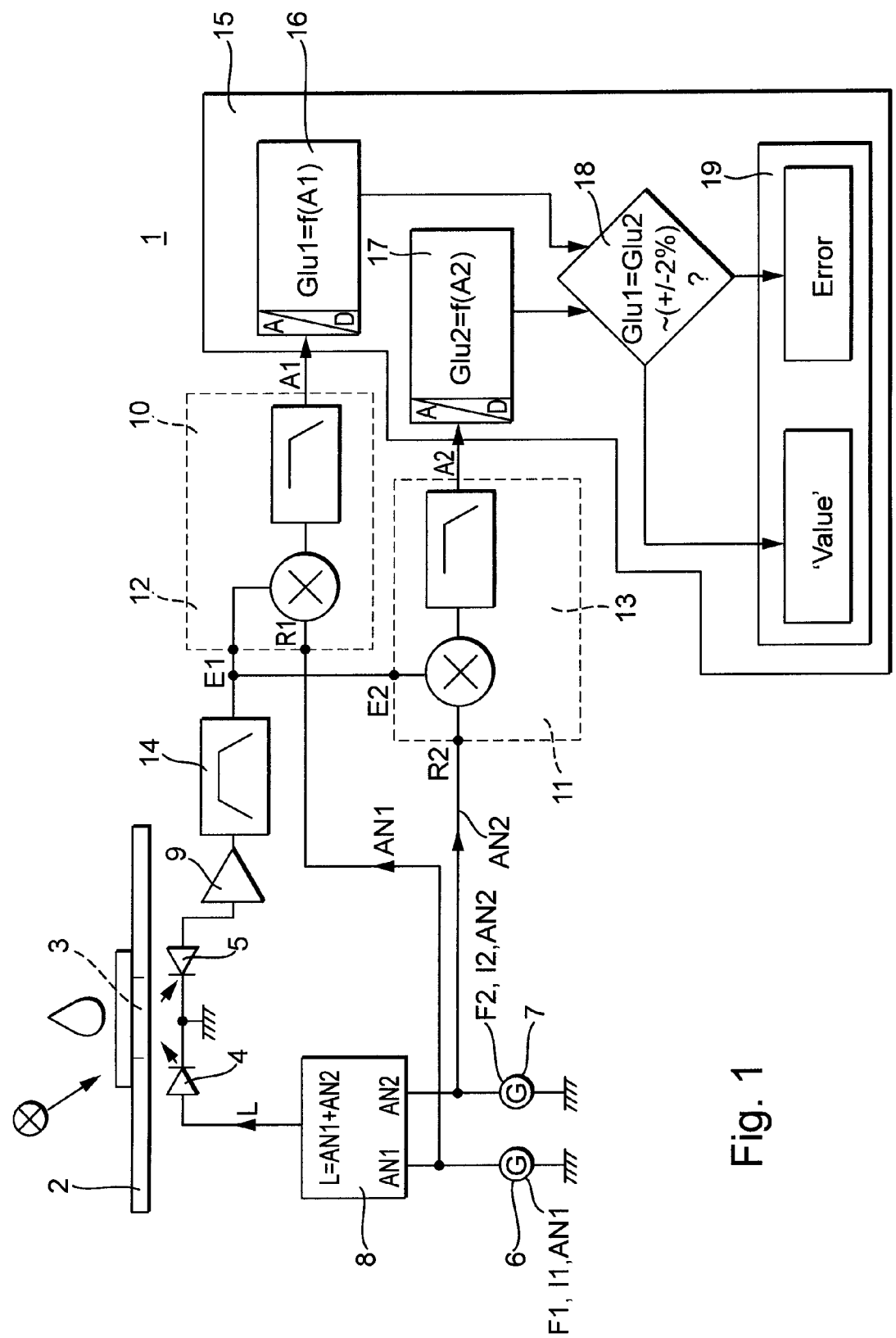
FIG. 1 is a schematic circuit diagram of a system according to the present invention for acquiring and evaluating photometric signals

The system according to a first embodiment of the present invention acquires and evaluates optical signals using a test carrier 2, which has a optical evaluation zone 3. The system comprises a light source 4 to illuminate the optical evaluation zone 3 on the test carrier 2 and a light sensor 5 to receive the light remitted from the optical evaluation zone 3 and convert it into a measuring signal. A first control signal AN1 having a frequency F1 and an intensity I1 and a second control signal AN2 having a frequency F2 and an intensity I2 are generated by separate signal generators 6, 7 or by the same signal generator 6. The system comprises a mixer unit 8 to generate a light control signal L from the first control signal AN1 and the second control signal AN2. The light source 4 is activated by the light control signal L.

The measuring signal received from the light sensor 5 as well as the first control signal AN1 of the first signal generator 6 and/or the second control signal AN2 of the second signal generator 7 are fed to a first frequency-selective amplifier 10 and a second frequency-selective amplifier 11 respectively. A first output signal A1 and a second output signal A2 respectively are outputted at the outputs of the amplifiers 10, 11. Both signals A1, A2 are compared in an evaluation unit 15. Information about interference of the measurement, in particular by external light, is determined from the result of the comparison.

The operation of the evaluation unit 15 can run in practice in such a manner that the result of the comparison of the output signals A1, A2 is compared to a predefined comparison result, which is to be expected with interference-free function (and otherwise identical conditions). In the simplest case, the two output signals A1, A2 are identical with interference-free function. The predefined comparison result is the correspondence of both signals A1, A2. However, there can also be a functional relationship between the two output signals A1, A2. In this case, the functional dependence is taken into consideration in the evaluation unit 15 by the predefined comparison result. For example, the value of the first output signal A1 can be a multiple of the value of the second output signal A2, in particular if the intensity of the first control signal A1 is a multiple of the intensity of the second control signal A2. The functional relationship between the output signals A1, A2 can also be given by a function other than proportionality.

The comparison performed in the evaluation unit 15 does not have to relate directly to the output signals A1, A2, but rather they can also be compared directly to one another. Examples are the comparison of referenced output signals A1, A2 and analytical results determined from the output signals A1, A2 using calibration data. Both will be explained in greater detail.

The information about interference of the measurement, in particular interference by external light, obtained on the basis of the comparison of the output signals A1, A2 can be used differently and processed further as a function of the type of the result ("interference-free" or "corrupted") and of other factors:

If interference exists, this information can particularly be processed to generate an error message, for example, as clear text on a display 19 or as another optical or acoustic signal. In addition, it can be used to block the further processing of the output signals A1, A2 into an analytical result.

However, the information obtained by the comparison can also be processed further as an internal control signal of the analysis system, whereby the output of an analytical result, for example, the measured glucose concentration, is released if the result of the comparison corresponds to the predefined comparison result.

Independently of the type of further processing, the signal resulting from the comparison operation, which contains information about the presence of interference, is referred to in the following as the "analysis signal".

The frequency-selective amplifier 10 is advisably set as much as possible in such a manner that it does not operate on the interfering frequency. The frequency of the interfering frequencies occurring is typically not entirely known, however. According to the present invention, a parallel measurement is performed. At least two measurements are performed simultaneously and exemplarily in one system. The two frequencies F1 and F2 of the control signals AN1, AN2 are contained in the light control signal L, which is generated in the mixer unit 8 from the first and second control signals AN1, AN2. These two frequencies F1 and F2 can be extracted again from the measuring signal output by the light sensor 5 and filtered out according to the present invention.

The light source 4 is activated using the light control signal L, which contains the two frequencies F1 and F2, resulting from the mixing. Two frequency-selective amplifiers 10, 11, which operate at the frequency F1, F2, respectively, are connected in parallel to evaluate the measuring signal, because they are activated using the first or second control signal AN1, AN2 as the reference signal. The effect of two bandpass filters connected in parallel having a filter band around the frequency F1 or F2 is thus practically achieved.

By connecting the two frequency-selective amplifiers 10, 11 in parallel, it can be recognized via a simple comparison whether an interfering signal is superimposed on the measuring signal. The risk that an interference will not be recognized only exists if the interference acts in both frequency ranges corresponding to the frequencies of the control signals AN1, AN2 at the equal intensity ratio, which the control signals AN1, AN2 have. This is very improbable. Because the interferences are typically relatively narrow-band, but in any case do not cover a broad frequency spectrum at equal intensity, interfering variables which occur are reliably recognized by the parallel connection of two frequency-selective amplifiers 10, 11.

The measurement becomes significantly more secure due to the reliable detection of an error. In particular for glucose determination in blood, a secure result which is free of interfering influences is important because further treatment for the patient is based on this measurement, e.g., the insulin dosing.

The production costs for a selective frequency amplifier are low at large piece counts. The overall costs of the measuring system rise only insignificantly due to the use of a second frequency-selective amplifier 11. Lock-in amplifiers 12, 13 are exemplarily used as the frequency-selective amplifiers 10, 11. These have the function of a very sharp frequency-selective filter, because only the frequency components of the measuring signal which correspond to the frequency of a reference signal AN1, AN2 are amplified.

In the event of multiple or permanent occurrence of interferences, the activation frequencies F1 and F2 of the control signals AN1, AN2 can be shifted into those ranges in which no interferences occur. For example, the frequencies F1 and F2 of the control signals AN1, AN2 are selected in the event of occurrence of a 50/60 hertz interfering voltage in such a manner that they are not equal to 50/60 hertz or a multiple thereof.

The term signal source is to be understood very generally in the scope of the present invention. In the simplest case, the signal source is a signal generator 6, for generating a control signal AN1, such as a sinusoidal signal, a trapezoidal signal, or a square-wave signal. The signal source can, however, also comprise two or more signal generators 6, 7, so that multiple control signals AN1, AN2 can be generated simultaneously in one signal source.

The first control signal AN1 is a square-wave signal having a fundamental frequency and the second control signal AN2 is a harmonic of the first control signal, whose frequency is a multiple of the fundamental frequency. The intensity I2 of the second control signal AN2 is different from the intensity of the first control signal AN1. The first and second control signals AN1, AN2 can be generated by the same signal generator 6. The frequency of the second control signal AN2 is an odd multiple of the fundamental frequency. The third harmonic of the square-wave signal, whose frequency corresponds to three times the fundamental frequency, is exemplarily used. The intensity of this harmonic is approximately a third of the intensity of the fundamental frequency, i.e., the intensity I2 is a third of the intensity I1.

In this way, a signal generator 6 which only generates a square-wave signal can be used as a signal source for two frequencies or two control signals AN1, AN2 having different frequencies (which are multiples of one another). Of course, the fifth and seventh harmonics are also suitable, the intensity decreasing with the degree of the harmonic (harmonic number). In particular, the higher harmonics (e.g., fifth and seventh harmonics) can additionally be generated if multiple control signals AN1, AN2 are to be generated because multiple frequency-selective amplifiers 10 are connected in parallel in the system for detecting the remitted light signals.

In another embodiment, the first output signal A1 is set in relation to a first reference signal in the analysis unit 16, whereby a first referenced output signal results. The same method is used for the second output signal A2, which is set in relation to a second reference signal in such a manner that a second referenced output signal is generated. The two referenced output signals A1, A2 are then related to one another, for example, by calculating a ratio. By using a reference signal, to which the output signal A1, A2 is set in relation (for example by division), oscillations in the measuring system are compensated for. This is the case in particular if the reference signal corresponds to the control signal which is generated using the signal generator 6. Oscillations or deviations of control signal are calculated out. The reference signals can also be generated by a "blank measurement" on an empty test carrier 2, to which no analysis liquid has been applied.

The frequency-selective amplifiers 10 are implemented in an electronic component. For example, ASICs may be used here. The production of a detection and evaluation apparatus for photometric signals is thus very cost-effective. It is also possible to implement the frequency-selective amplifiers 10 in software which runs in the same electronic component. In this case, if the signal is not amplified by hardware, an A/D converter is to be used, which converts the analog signal into a digital signal. Multiplications are then performed by software. In this manner, no additional costs arise due to an additional lock-in amplifier 12, because no additional hardware needs to be implemented. The production costs are reduced. Miniaturization of the system is possible.

In another embodiment, a third control signal AN3 (not shown) and a third frequency-selective amplifier (not shown) are provided. The third control signal AN3 has a frequency F3 and an intensity I3. The light control signal L for activating the light source 4 is generated from the first, second, and third control signals AN1, AN2, AN3. The measuring signal of the light sensor 5 and the third control signal AN3 are also fed to the third frequency-selective amplifier, which is connected to the other two amplifiers 10, 11 in parallel. A third output signal A3 is outputted at the output of the third frequency-selective amplifier, which is fed to the analysis unit 16 in addition to the first output signal A1 and the second output signal A2 and is compared thereto. If a deviation of an output signal A1, A2, A3 is detected, the resulting interference information is used so that the deviating output signal A1, A2, A3 is not taken into consideration.

If an interfering signal occurs, i.e., an error is recognized, one output signal A1, A2, A3 deviates from the other two. The other two output signals A1, A2, A3 are identical. In this case, it is thus recognized that the deviating output signal A1, A2, A3 has an interfering variable superimposed. The two identical output signals A1, A2, A3 represent the "correct", i.e., error-free measuring result. Thus, a statement can be made as to whether an error has occurred, and the two other output signals A1, A2, A3 can be processed further to determine the desired analytical result (concentration of the analyte in the analysis liquid). Of course, this can be expanded to embodiments having multiple selective amplifiers, e.g., having N amplifiers (N>2, N integral). In this case, if interference only occurs on the frequency of one control signal, the other N−1 output signals are identical. The so-called "majority logic" is applied.

Again, FIG. 1 shows a blood sugar measuring device as an analysis device 1 for acquiring an analyte. The glucose content in a sample liquid, in particular in blood, is measured using the blood sugar measuring device. A test carrier 2 is implemented as a test strip, onto which blood is placed as the analysis liquid, which contains the analyte, glucose, to be investigated. An optical evaluation zone 3 of the test carrier 2 is illuminated by a light source 4 of the analysis device 1. The light source 4 is a light-emitting diode. Of course, multiple arbitrary light sources can also be provided, which can be connected in parallel or in series. The light emitted from the evaluation zone 3 is received by a light sensor 5, which is implemented as a photodiode.

The light source 4 is activated by a first signal generator 6 and a second signal generator 7. The two signal generators 6, 7 each generate a signal having a fixed frequency and predefined intensity. The first signal generator 6 generates a control signal AN1 having the frequency F1 and the intensity I1. The second signal generator 7 generates an control signal AN2 having the frequency F2 and the intensity I2. The particular control signals AN1, AN2 of the two signal generators 6, 7 are fed to a mixer unit 8, in which a light control signal L is generated. The light control signal L is produced from the first control signal AN1 of the first signal generator 6 and the second control signal AN2 of the second signal generator 7, for example, by mixing. In particular, the first control signal AN1 and the second control signal AN2 can be added to one another in the mixer unit 8. The light control signal L is fed to the light source 4 to activate it.

The frequency components of the light control signal L, i.e., of the first control signal AN1 and the second control signal AN2 are contained in the light component diffusely reflected from the optical evaluation zone 3 (test panel), which is emitted from the light source 4 onto the optical evaluation zone 3 and received by the light sensor 5. The light signal received by the light sensor 5 is converted into a photocurrent. The photocurrent is converted into a voltage and amplified in a preamplifier 9. The output signal of the preamplifier 9 is fed in parallel to a first frequency-selective amplifier 10 and a second frequency-selective amplifier 11. The frequency-selective amplifiers 10, 11 are implemented as lock-in amplifiers 12 and 13.

A filter is optionally provided between the light sensor 5 and the frequency-selective amplifiers 10, 11, which is exemplarily implemented as a bandpass filter 14. The bandpass filter 14 is positioned between the preamplifier 9 and the frequency-selective amplifier 10 or 11. The bandpass filter 14 limits the output signal of the preamplifier 9 to a frequency range, which contains the frequencies F1, F2 of the first control signal AN1 and the second control signal AN2. The bandpass filter 14 is optionally integrated in the preamplifier 9. Alternatively, a low-pass filter can also be integrated in the preamplifier 9. The downstream bandpass filter 14 can then be replaced by a high-pass filter. Overall, a bandpass filter 14 is connected before the lock-in amplifiers 12, 13 in any case.

The filtered signal of the preamplifier 9 is fed to the input E1 of the first lock-in amplifier 12 and the input E2 of the second lock-in amplifier 13. The control signal AN1 of the first signal generator 6 is applied to a reference input R1 of the lock-in amplifier 12. The second control signal AN2 of the second signal generator 7 is applied to a reference input R2 of the second lock-in amplifier 13.

The output signals A1, A2 are fed to an evaluation unit 15, in which they are compared. A corresponding evaluation signal is outputted at the evaluation unit 15. The evaluation signal is displayed on a display 19 or is transformed as a data value or signal to a processing device (e.g., a computer), for example.

The analysis device 1 exemplarily has two and only two frequency-selective amplifiers 10, 11 as shown in FIG. 1. In the case of precisely two frequency-selective amplifiers 10, 11, a faultily performed measurement is recognized by direct comparison of the deviation of the output signal A1 of the first amplifier 10 and the output signal A2 of the second amplifier 11. If the intensities I1, I2 of the two control signals AN1, AN2 of the first signal generator 6 and the second signal generator 7, respectively, are identical, the output signals A1, A2 of the lock-in amplifiers 12, 13 are also identical.

The intensities of the particular control signals of the signal generators may be different. The intensity I1 of the control signal AN1 of the first signal generator 6 and the intensity I2 of the control signal AN2 of the second signal generator 7 have a specific ratio. The two output signals A1, A2 of the lock-in amplifiers 12, 13 have the same ratio (predefined or rated comparison result) to one another. To check this, they are set in relation to one another. If the identical ratio is not provided, interference of the measurement, for example, by scattered light or ambient light, is detected.

A first and a second analytical result are derived, in each case by means of calibration data, in the evaluation unit 15 from the first output signal A1 and from the second output signal A2. The two analytical results are concentration values of the analyte which is contained in the analysis liquid on the optical evaluation zone 3 of the test carrier 2. For this purpose, the evaluation unit 15 includes an analysis unit 16 and an analysis unit 17. To calculate the analytical results, the calibration data is stored in the analysis units 16, 17, for example as a mathematical function which reflects the relationship between the output signal and the analytical result.

The analysis units 16, 17 each have an analog-digital converter (A/D converter) at their input. The output signals A1 and A2 of the lock-in amplifiers 12, 13 applied to the inputs of the analysis units 16, 17 are converted into digital signals, such that digital signals can be processed subsequently in the evaluation unit 15. If the two lock-in amplifiers 12, 13 are implemented in the software, the A/D converters at the inputs of the analysis units 16, 17 can be dispensed with. However, in this case the A/D converter is provided directly at the output of the bandpass filter 14. The output signal of the bandpass filter 14 is digitized so that digital signals are provided at each of the inputs E1, E2 of the lock-in amplifiers 12, 13. In this case, only one A/D converter has to be provided, in contrast to two, if the lock-in amplifiers 12, 13 are implemented in the form of hardware components.

If the analysis device 1 is a blood sugar measuring device as here and the analyte to be determined is the glucose content in the blood, the analytical results which are determined by means of the analysis unit 16 or 17 are values of the glucose content in the blood. For example, the system can be calibrated in such a manner that a liquid having a known glucose content is applied to the test strip and the output signals A1, A2 of the lock-in amplifiers 12, 13 are determined. This value is used as the calibration value. This may also be performed in a production processing step and is then stored as a function on the test strip 2. The information is stored and/or implemented in the analysis units 16, 17. The calibration is performed at different glucose concentrations and at different frequencies, and multiple sets of calibration data being obtained. In the simplest case, the data is stored in a table which the analysis units 16, 17 can access. Intermediate values are determined by interpolation. The more extensive the calibration data base, the more precisely the glucose value contained in the analysis liquid can be concluded from the output signals A1, A2 of the lock-in amplifiers 12, 13.

The analytical results of the analysis units 16, 17 are compared to one another in a comparator 18. The result of the comparison is visually displayed to the user of the analysis device 1, for example, in a display 19. If analytical results are compared, the predefined comparison value corresponds to the correlation of the results. Differences of the output signal of the lock-in amplifiers 12 are compensated for by the calibration. If the two analytical results are identical, the measured glucose value is displayed in the display 19; otherwise, an error message is outputted. The output can be text, an optical signal, or an acoustic output.

It has been shown suitable not to compare the output signals of the frequency-selective amplifiers 10 directly as raw data, but rather to determine the analytical results determined from this raw data and compare them to one another such that the output signals are related indirectly to one another. Thus, errors in the electronics during the evaluation of the output signals A1, A2 of the lock-in amplifiers 12, 13 can also be taken into consideration. In particular, if the analysis device 1 is implemented by means of microprocessors, errors are recognized, which originate from a defect of the microprocessors. Although such errors are very rare, they can be precluded easily if the analytical results, and not the output signals A1, A2 of the lock-in amplifiers 12, 13, are compared to one another.

Using a further lock-in amplifier and accordingly a further control signal has the result that not only is an interfering influence on the measurement recognized, but additionally, in spite of the interference, a correct analysis result can be outputted. The probability that interference will interfere the measurement simultaneously and in the same manner at two or more frequencies is very small. This probability is reduced even further by adding further lock-in amplifiers. In particular if the lock-in amplifiers are implemented in software, the constructive effort is so small that multiple lock-in amplifiers can also be used to increase the security of the result further.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

The invention claimed is:

1. An optical measuring device for detecting an analyte in an analysis liquid disposed on a test carrier which has an optical evaluation zone, the device comprising:
    a first signal generator for generating a first control signal having a first frequency and a first intensity,
    a second signal generator for generating a second control signal having a second frequency and a second intensity,
    a light source for illuminating the optical evaluation zone using a light control signal based on the first and second control signals;
    a light sensor for receiving light from the optical evaluation zone and for converting the received light into a measuring signal;
    a first frequency-selective amplifier, to which the measuring signal and the first control signal are fed and having an output for outputting a first output signal,
    a second frequency-selective amplifier, to which the measuring signal and the second control signal are fed and having an output for outputting a second output signal,
    an evaluation unit, to which the first output signal and the second output signal are fed, the evaluation unit being configured to compare the first output signal and the second output signal and to derive information about interference of the measuring signal based on the comparison.

2. The device of claim 1, further comprising a mixer unit for generating, from the first control signal and the second control signal, a light control signal for controlling light emission of the light source.

3. The device of claim 1, wherein the first and second signal generators are implemented in the same electronic component.

4. The device of claim 1, further comprising a signal source for generating a third control signal having a third frequency and a third intensity, a light control signal being generated by a mixer unit from the first control signal, the second control signal, and the third control signal, a third frequency-selective amplifier, to which the measuring signal and the third control signal of the third signal generator are fed and having an output for outputting a third output signal, and
    the evaluation unit being fed with the third output signal and being adapted for comparing the first output signal, the second output signal and the third output signal.

5. The device of claim 4, wherein the evaluation unit includes circuitry and programming to determine if one or more of the first, second, and third output signals are errant.

6. The device of claim 5, wherein the evaluation unit includes circuitry and programming to determine whether at least two of the first, second, and third output signals are consistent with each other.

7. The device of claim 1, wherein precisely two frequency-selective amplifiers are provided and in the event of deviation of the two output signals from a predefined comparison result, the measurement performed is recognized as faulty.

8. The device of claim 1, wherein the intensities of the first and second control signals are different.

9. The device of claim 1, wherein the first control signal is a square-wave signal having a fundamental frequency and the second control signal is a harmonic of the first control signal, the frequency of the second control signal being a multiple of the fundamental frequency, and the intensity of the second control signal being different from the intensity of the first control signal.

10. The device of claim 9, wherein the frequency of the second control signal is three times the fundamental frequency.

11. The device of claim 1, wherein the evaluation unit calculates a ratio of the first output signal and a first reference signal for generating a first referenced output signal, calculates a ratio of the second output signal and a second reference signal, for generating a second referenced output signal, and compares the first referenced output signal to the second referenced output signal.

12. The device of claim 1, wherein a first analytical result is derived in the evaluation unit from the first output signal using first calibration data, a second analytical result is derived in the evaluation unit from the second output signal using second calibration data, and the first and second analytical results are compared to obtain the information about interference of the measurement.

13. The device of claim 1, wherein a bandpass filter is located between the light sensor and the first frequency-selective amplifier.

14. The device of claim 1, wherein the first frequency-selective amplifier is software implemented in an electronic component.

15. The device of claim 1, wherein the frequency-selective amplifiers are implemented in the same electronic component.

16. A method for measuring and evaluating photometric signals for detecting an analyte in an analysis liquid, comprising the following steps:
    illuminating an optical evaluation zone of a test carrier by a powered light source,
    receiving the light remitted from the optical evaluation zone by a light sensor,
    converting the light received by the light sensor into a measuring signal,
    generating a first control signal having a first frequency and a first intensity,
    generating a second control signal having a second frequency and a second intensity,
    generating a light control signal from the first control signal and the second control signal for activating the light source,
    feeding the measuring signal received from the light sensor to a first frequency-selective amplifier and to a second frequency-selective amplifier, feeding the first control signal to the first frequency-selective amplifier and feeding the second control signal to the second frequency-selective amplifier, feeding a first output signal of the first frequency-selective amplifier and a second output signal of the second frequency-selective amplifier to an evaluation unit, comparing the first output signal to the second output signal in the evaluation unit, and determining information about the measuring signal from the result of the comparison.

17. The method of claim 16, wherein the first control signal is generated by a first signal generator and the second control signal is generated by a second signal generator.

18. The method of claim 16, further including the steps of generating the first output signal by calculating a ratio of the first output signal and a first reference signal, and generating the second output signal by calculating a ratio of the second output signal and a second reverence signal.

19. The method of claim 16, wherein the first control signal is a square-wave signal having a fundamental frequency and the second control signal is a harmonic of the first control signal, the frequency of the second control signal being a multiple of the fundamental frequency, and the intensity of the second control signal being different from the intensity of the first control signal.

20. The method of claim 16, wherein the comparing step includes:

deriving a first analytical result in the evaluation unit from the first output signal using first calibration data, deriving a second analytical result in the evaluation unit from the second output signal using second calibration data, and comparing the first and second analytical results to obtain the information about the measuring signal.

21. The method of claim 16, wherein the determined information relates to interference due to external light.

* * * * *

UNITED STATES PATENT AND TRADEMARK OFFICE
CERTIFICATE OF CORRECTION

| | | |
|---|---|---|
| PATENT NO. | : 7,630,084 B2 | Page 1 of 1 |
| APPLICATION NO. | : 11/871185 | |
| DATED | : December 8, 2009 | |
| INVENTOR(S) | : Frederic Wehowski, Bernd Rösicke and Stefan Kalveram | |

It is certified that error appears in the above-identified patent and that said Letters Patent is hereby corrected as shown below:

Title Page, item (75); should read;

Bernd Rösicke

Signed and Sealed this
Seventeenth Day of April, 2012

David J. Kappos
*Director of the United States Patent and Trademark Office*